United States Patent
Carlsson et al.

(10) Patent No.: US 10,478,402 B2
(45) Date of Patent: *Nov. 19, 2019

(54) SOLID NANOPARTICLE WITH INORGANIC COATING

(71) Applicant: Nanexa AB, Uppsala (SE)

(72) Inventors: Jan-Otto Carlsson, Uppsala (SE); Anders Johansson, Uppsala (SE); Marten Rooth, Knivsta (SE)

(73) Assignee: Nanexa AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,073

(22) Filed: Jul. 10, 2017

(65) Prior Publication Data

US 2018/0085321 A1 Mar. 29, 2018

Related U.S. Application Data

(63) Continuation of application No. 14/891,398, filed as application No. PCT/EP2014/060746 on May 23, 2014, now abandoned.

(30) Foreign Application Priority Data

May 24, 2013 (EP) .................................... 13169219

(51) Int. Cl.
*A61K 9/50* (2006.01)
*A61K 9/51* (2006.01)

(52) U.S. Cl.
CPC .......... *A61K 9/5192* (2013.01); *A61K 9/5073* (2013.01); *A61K 9/5115* (2013.01)

(58) Field of Classification Search
CPC ... A61K 9/5073; A61K 9/5115; A61K 9/5192
See application file for complete search history.

(56) References Cited

U.S. PATENT DOCUMENTS

| | | | |
|---|---|---|---|
| 5,753,023 A * | 5/1998 | Bishop .................. | C09C 1/0015 106/31.65 |
| 7,459,145 B2 * | 12/2008 | Bao ..................... | A61K 49/0002 424/1.11 |
| 7,678,429 B2 | 3/2010 | Goodwin et al. | |
| 7,858,144 B2 * | 12/2010 | Freeman ............... | C23C 16/545 117/88 |
| 8,097,742 B2 | 1/2012 | Ying et al. | |
| 8,426,489 B1 * | 4/2013 | Al-Haik ................ | A61L 27/443 433/192 |
| 2007/0061006 A1 | 3/2007 | Desatnik et al. | |
| 2007/0238311 A1 * | 10/2007 | Levy .................... | C23C 16/403 438/765 |
| 2009/0186068 A1 | 7/2009 | Miller et al. | |
| 2009/0324676 A1 | 12/2009 | Hofmann et al. | |
| 2010/0016443 A1 | 1/2010 | Toledano et al. | |
| 2011/0022160 A1 | 1/2011 | Flanagan et al. | |
| 2011/0054633 A1 | 3/2011 | Miller et al. | |
| 2011/0104073 A1 * | 5/2011 | Zeng .................. | A61K 41/0052 424/9.32 |
| 2012/0201860 A1 | 8/2012 | Weimer et al. | |
| 2013/0059073 A1 * | 3/2013 | Jiang .................. | C23C 16/4417 427/212 |
| 2015/0250731 A1 | 9/2015 | Hoppu et al. | |

FOREIGN PATENT DOCUMENTS

| | | | | |
|---|---|---|---|---|
| CN | 102330051 A | 1/2012 | | |
| EP | 1 757 251 A1 | 2/2007 | | |
| EP | 1757271 A1 * | 2/2007 | .......... | A61K 9/1676 |
| JP | 2010006780 A | 1/2010 | | |
| JP | 2010-059005 A | 3/2010 | | |
| WO | 2003/086030 A1 | 10/2003 | | |
| WO | 2010/076803 A2 | 7/2010 | | |
| WO | WO-2010076803 A2 * | 7/2010 | .............. | A61K 8/11 |
| WO | 2011/057937 A2 | 5/2011 | | |
| WO | 2012/116814 A1 | 9/2012 | | |
| WO | 2015/067763 A1 | 5/2015 | | |

OTHER PUBLICATIONS

Arruebo, "Drug delivery from structured porous inorganic materials", WIREs Nanomedicine and Nanobiotechnology, vol. 4, Jan./Feb. 2012, pp. 16-30.
Knez et al., "Atomic Layer Deposition on Biological macromolecules: Metal Oxide Coating of Tobacco Mosaic Virus and Ferritin", Nano Letters, vol. 6, No. 6, 2006, pp. 1172-1177.
Hyde et al., "Atomic layer deposition of titanium dioxide on cellulose acetate for enhanded hemostasis", Biotechnology Journal, vol. 6, 2011, pp. 113-223.
Lee et al., "Low-temperature ZnO atomic layer deposition on biotemplates: flexible photocatalytic ZnO structures from eggshell membranes", Physical Chemistry Chemical Physics, vol. 11, 2009, pp. 3608-3614.
Guo et al., "GaN Nanowire Functionalized with Atomic Layer Deposition Techniques for Enhanced Immobilization of Biomolecules", Langmuir Article, vol. 26, No. 23, 2010, pp. 18382-18391.
Korhonen et al., "Inorganic Hollow Nanotube Aerogels by Atomic Layer Deposition onto Native Nanocellulose Templates", ACS NANO, vol. 5, No. 3, 2011, pp. 1967-1974.
International Search Report for corresponding International Application No. PCT/EP2014/060746 dated Jun. 25, 2014.
Written Opinion of the International Search Authority for corresponding International Application No. 060746 dated Jun. 25, 2014.
Sivasankar et al., "Role of Nanoparticles in Drug Delivery System", International Journal of Research in Pharmaceutical and Biomedical Sciences, vol. 1 (2), Dec. 2010, pp. 41-66.
Dillon et al, "Surface chemistry of Al2O3 deposition using Al(CH3)3 and H2O in a binary reaction sequence", Surface Science 322, 1995, pp. 230-242.

(Continued)

*Primary Examiner* — Robert A Wax
*Assistant Examiner* — Olga V. Tcherkasskaya
(74) *Attorney, Agent, or Firm* — Pepper Hamilton LLP

(57) ABSTRACT

A nanoparticle having a solid core comprising a biologically active substance, said core being enclosed by an inorganic coating, a method for preparing the nanoparticle, and the use of the nanoparticle in therapy. A kit comprising the nanoparticle and a pharmaceutical composition comprising the nanoparticle.

29 Claims, 4 Drawing Sheets

(56) References Cited

OTHER PUBLICATIONS

Ott et al., "Al3O3 thin film growth on Si(100) using binary reaction sequence chemistry", Thin Solid Films 292, 1997, pp. 135-144.
Tsapatsis et al., "Synthesis of Hydrogen Permselective SiO2, TiO2, Al2O3, and B2O3 Membranes from the Chloride Precursors", Ind. Eng. Chem. Research, vol. 30, No. 9, 1991, pp. 2152-2159.
Lin et al., "CVD of Solid Oxides in Porous Substrates for Ceramic Membrane Modification", AIChE Journal, vol. 38, No. 3, pp. 445-454.
Kumaresan et al., "Dry Powder Inhaler—Formulation aspects", Pharma Times, vol. 44, No. 10, Oct. 2012, pp. 14-18.
Mack et al., "Particle engineering for inhalation formulation and delivery of biotherapeutics", Inhalation, vol. 6, No. 4, Aug. 2012, pp. 16-20.
Raula et al. "A novel gas phase method for the combined synthesis and coating of pharmaceutical particle", Pharmaceutical Research 25.1, 2007, pp. 242-245.
Feil et al., "Nanoparticle based inorganic coatings for corrosion protection of magnesium alloy," Surface Engineering 24.3, 2008), pp. 198-203.
Hakim et al., "Conformal nanocoating of zirconia nanoparticles by atomic layer deposition in a fluidized bed reactor", Nanotechnology, vol. 16, 2005, pp. S375-S381.
Van Ommen et al., "Fluidization of nanopowders: a review", J Nanopart Res, 2012, 14:737, pp. 1-29.

\* cited by examiner

SOLID NANOPARTICLE WITH INORGANIC COATING

This application is a continuation of U.S. application Ser. No. 14/891,398 filed on Nov. 16, 2015, which is a national phase of International Application No. PCT/EP2014/060746 filed May 23, 2014 and published in the English language, which claims priority to Application No. EP 13169219.6 filed May 24, 2013.

FIELD OF THE INVENTION

The present invention relates to the field of nanoparticle technology. In particular, the invention relates to solid nanoparticles for use in the pharmaceutical field, e.g. for drug delivery.

BACKGROUND OF THE INVENTION

Many of today's drugs are formulated in the solid state and an often encountered problem is the poor water solubility of such drugs, which not only renders the drug difficult to formulate, but also may pose an obstacle to an adequate biodistribution in the body of the patient. Various methods have been developed for enhancing the bioavailability of such poorly soluble drugs. One method is to formulate the drug in nanoparticulate form.

With a decrease in particle size, and a consequent increase in ratio of surface area/mass, the rate of dissolution is enhanced. While the small size scale of the particles is considered to enhance dissolution rate, there still may be a problem of allowing the particle to reach its desired target in the body before dissolution takes place. Furthermore, while generally it is considered that the small size of the particles will allow the particles to penetrate barriers such as cell membranes within the human and animal body, targeted delivery nonetheless generally requires the particles to be provided with adequate surface functionalizations and terminations, in addition to protection against premature dissolution or disintegration in the body.

Generally, particles having a size of from 0.1 μm (micrometer), i.e. 100 nm (nanometers) to 100 μm, i.e. 100 000 nm, are classified as microparticles, whereas particles having a size of from 1 nm to 100 nm are generally defined as nanoparticles. For the purpose of the present invention, the term "nanoparticle" will be used to designate both types of particles, unless otherwise specifically indicated or apparent from the context.

There is an ever increasing demand of advanced and controlled drug delivery, i.e., use of formulation components and devices to release a therapeutic agent at a predictable rate in vivo when administered by an injected or non-injected route.

Some drugs have an optimum concentration range and the controlled delivery should be designed for that range to achieve effective therapies and also reducing/eliminating potential for both under- and overdosing. Besides keeping the drug concentration in the body constant for a long time, there might be needs of cycling the delivery over a long period of time or trigger drug release. Finally, effectiveness of a drug and cellular uptake can be improved considerably by functionalizing and attachment of target molecules to the drug molecules.

The direct delivery of drugs and biomolecules is generally inefficient and can seldom meet the requirements mentioned above. Hence, more effective drug transport and release systems, including different kinds of vehicles, have been designed and used. Polymers, liposomes, dendrimers and micelles are all examples of such vehicles.

A significant proportion of drugs on the market are poorly soluble in water, and it is expected that this will be even more pronounced in the future. Formulations of poorly water-soluble compounds offer a challenge to the formulation experts, from the early discovery phase through the development to the launch of the pharmaceutical product.

A frequently overlooked alternative to conventional vehicles are nanoparticles. However, there are some problems with the use of nanoparticles as a drug vehicle, such as particle aggregation and Ostwald ripening (growth of bigger particles at the expense of the smaller ones).

SUMMARY OF THE INVENTION

It is an object of the present invention to provide a versatile controlled drug delivery system meeting the requirements mentioned above. The drug delivery system of the present invention is based on an inorganic capsule, preferably an oxide, that totally encapsulates the drug. The thickness of the layer can be varied and controlled down to a monolayer of atoms, meaning that the drug release can be controlled with the layer thickness. By making a blend of drug vehicles with different layer thicknesses a desired drug release profile can be designed.

Some advantages of the drug delivery system of the present invention are the possibility of providing:
  controlled drug release over longer times and even cyclic, making efficient use of drugs as well as reducing side effects;
  capacity of of tailoring surface properties and size of the drug vehicle for targeting of different substances, enabling the vehicles to pass barriers like the blood-brain, placenta and gastrointestinal barriers;
  poorly water-soluble drugs can be transformed to water-soluble by applying a thin and completely intact layer of an appropriate oxide;
  an extremely high drug load can be achieved, usually higher than 80%;
  solid drugs can advantageously be used;
  the encapsulating material is biodegradable;
  the formulation routes of drugs can be standardized since different kinds of drug particles can be provided with the same layer or shell, facilitating the handling of drug and reducing formulation cost;
  the shelf life can be prolonged due to the encapsulation;
  the whole drug delivery system is composed of constituents that are easily excreted from the body of the treated subject after a relative short period of time.
  the drug release time can be varied over a wide range (from minutes to week).

During the process of developing a nanoparticle based drug delivery system, the present inventors prepared nanoparticles comprising a solid core and an inorganic coating and subjected them to various tests.

In contact with a solvent the nanoparticles however generally were found to dissolve too rapidly, thereby being unsuitable for controlled delivery of the active ingredient present in the solid core.

Several hypotheses for this unsatisfactory behaviour were put forward and numerous tests were made. As a result, the inventors found that the unsatisfactory dissolution profile was due to an incomplete coverage of the particle surface. Indeed, the inventors found that after applying the inorganic coating to the nanoparticles using conventional Atomic Layer Deposition (ALD), each solid core was only partially coated and the coating was interrupted by holes, even when submitting the nanoparticles to several ALD coating steps.

The inventors surmised that the disruptions (holes) in the coating might correspond to points of contact between the particles during the application of the coating. To verify this hypothesis, the nanoparticles were again submitted to several ALD coating steps, and in between each coating, the particles were submitted to sonication. The sonication treatment resulted in an agitation of the particles, which in turn led to a disaggregation of the nanoparticles. In the subsequent coating step, the probability was high that each particle would present at least partly a different surface to the ALD coating treatment, and at least part of the contact holes at the surface of any one particle would thus become covered in the subsequent treatment. By repeating the steps of agitation and surface coating, a plurality of particles finally was obtained wherein at least some of the particles were covered by an integral surface coating.

The nanoparticles obtained by such a repeated treatment were found to show an excellent profile of delayed release of the active substance present in the solid core.

Thus, it was realized that in order to have a non-interrupted coating enclosing completely the solid core, application of inorganic material must be performed by a method including an agitation treatment of the particles, either intermittently or continuously.

A first aspect therefore is a method of preparing a coated nanoparticle having a core enclosed by an in inorganic coating, the core comprising a biologically active substance; the method comprising applying one or more layers of inorganic material to a plurality of said solid cores by an application method wherein the inorganic material, or precursors for forming the inorganic material, is/are present in gas phase, and submitting said solid cores to agitation during and/or in between application of the layer(s) of inorganic material.

Thus, the method of applying the inorganic material coating to the solid core is a so-called gas phase technique.

In the method of the invention, the solid cores are not present in a liquid phase during the application of inorganic material, i.e. the method may be referred to as a gas phase method. In other words, in the coating method of the present invention, the inorganic material or precursors for forming the inorganic material is/are present in gas phase.

In some embodiments, more than one layer of inorganic material is applied to the solid cores and the solid cores are submitted to agitation after applying at least one layer of inorganic material and before applying at least one subsequent layer of inorganic material.

In one embodiment, the method of the invention comprises (i) applying inorganic material to a plurality of solid cores comprising a biologically active substance, (ii) submitting the plurality of solid cores to agitation, (iii) repeating step (i) at least once.

In one embodiment, the method of the invention comprises (i) applying inorganic material to a plurality of the solid cores, (ii) submitting the plurality of said solid cores to agitation, (iii) repeating step (i) n times, wherein n is an integer of at least 1, and (iv) when n is an integer of at least 2, repeating step (ii) after at least some of the steps (i).

For example, n may be 2, 3, 4, 5, 6, 7, 8 or 9, and may even be as high as, e.g., 10, 20, or 30, 40 or 50 or higher.

In a second aspect there is provided a plurality of nanoparticles, each having a solid core comprising a biologically active substance, said core being enclosed by an inorganic coating.

The plurality of nanoparticles of the invention may be used in various applications. For example, according to one aspect, when the biologically active substance is a drug, the nanoparticles of the present inventions are provided for use in therapy. In view of this, the invention also relates to a pharmaceutical composition comprising a plurality of therapeutically useful nanoparticles according to the invention and a pharmaceutically acceptable carrier.

Another aspect of the invention is a method of preparing a pharmaceutical composition, said method comprising combining a plurality of therapeutically useful nanoparticles according to the invention and a pharmaceutically acceptable carrier.

In some embodiments, the nanoparticle comprises one or more intermediary layers of a chemical composition different from that of the solid core, at the interface between the solid core and the inorganic coating.

In some further embodiments, the nanoparticle comprises one or more chemical moieties attached to the outer surface of the inorganic coating.

In some embodiments, the step of applying inorganic material to a plurality of the solid cores, comprises (a) introducing a first precursor, which is in a gaseous state, into a reactor pre-filled with the solid nanoparticles (the solid cores) to be coated;

(b) purging and/or evacuating the reactor to remove the non-reacted or non-adsorbed precursor and the gaseous reaction by-products;

(c) exposing the nanoparticles to a second precursor to activate the surface again for the reaction of the first precursor;

(d) purging and/or evacuating of the reactor and optionally repeating the steps (a) to (d) in order to achieve the desired coating thickness.

This is a general ALD process, well-known to the person of ordinary skill in the art. The steps a-d represent a reaction cycle or just cycle.

In some embodiments, the method comprises processing a biologically active substance, e.g. by micronizing, so as to provide a nanoparticle as a solid core to be coated, said core containing or consisting of the biologically active substance.

In some embodiments, the method comprises applying a surface treatment to the solid core prior to applying the inorganic coating to the surface of the solid core.

In some further embodiments, the surface treatment comprises applying one or more layers of a chemical composition different from that of the solid core.

In some further embodiments, the method comprises derivatizing or functionalizing the nanoparticle by attaching one or more chemical moieties to the outer surface of the inorganic coating.

According to a further aspect a pharmaceutical formulation is provided, comprising a plurality of nanoparticles according to the invention.

According to a still further aspect, a nanoparticle is provided, comprising a solid, biologically active compound, said nanoparticle having an inorganic surface coating, for use in therapy.

According to a still further aspect, a kit is provided, comprising a nanoparticle according to the invention.

Further aspects and embodiments of the invention will be apparent from the following description and the appended claims.

DETAILED DESCRIPTION OF THE INVENTION

Figure 1:
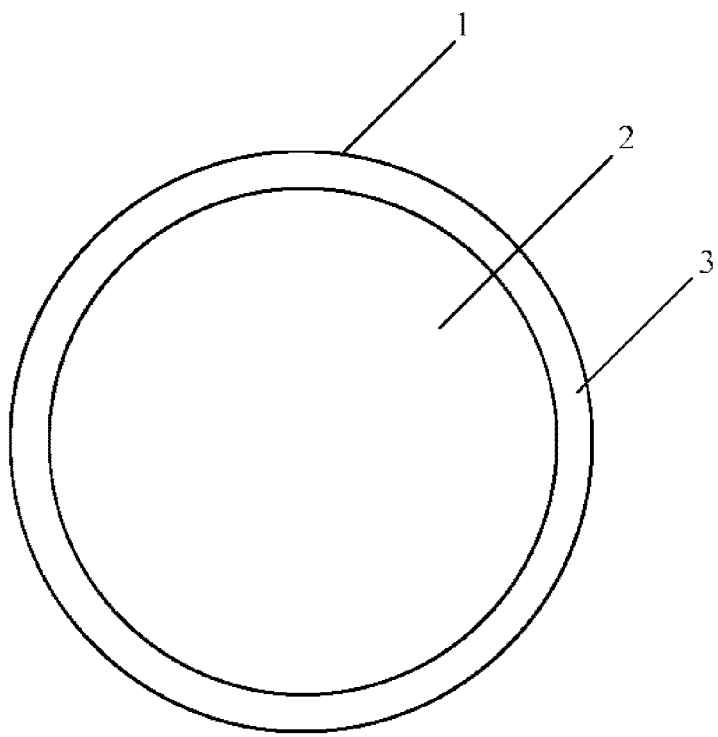
FIG. 1 illustrates a nanoparticle of the invention, having a core comprising a biologically active substance, said core being surrounded by an inorganic coating.

The nanoparticle of the invention is comprised of solid core formed by or comprising a biologically active substance, said core being surrounded by an inorganic coating. The inorganic coating may be applied directly to the outer surface of the solid core, without any intermediate layers, or may be applied to one or more intermediate layers at the surface of the solid core.

The nanoparticle, comprising the core, the inorganic coating and optionally any intermediate layers in between, has a size, expressed as the diameter of the particle, generally ranging from a few nanometers, e.g. 1-10 nm, to about 50 µm. In some embodiments, the nanoparticle has size ranging from 10 nm, or 20 nm, or 40 nm, to 1000 nm, or 500 nm, or 200 nm, or 100 nm, or 50 nm. For example, the nanoparticle may have a size ranging from 1 nm to 1000 nm, or from 10 nm to 200 nm, e.g. from about 50 nm to 200 nm. In some embodiments, the nanoparticle has a size of about 100 nm. In some other embodiments, the nanoparticle has a size of from about 10 nm to about 100 nm. In still other embodiments, the nanoparticle has a size of from about 100 nm to about 50 µm, e.g. about 1 µm to about 50 µm, or about 10 µm to about 50 µm, such as about 20 µm to 50 µm. The particle size may be determined using methodology and instrumentation well-known to the person of ordinary skill within the field, e.g. instruments as sold by Malvern Instruments Ltd.

The form of the nanoparticle may suitably be spherical or essentially spherical, but any other form is also possible, e.g. irregular, needle shaped or cuboid shaped, essentially depending e.g. on the method of preparation of the nanoparticle core. For a non-spherical particle, the size may be indicated as the size of a corresponding spherical particle of e.g. the same weight, volume or surface area. An advantageous feature of the method of the invention is the possibility of encapsulating also particles of very irregular shapes, and even particles having pores, crevices etc.

In some embodiments, the coating is applied directly onto the particle core. In some other embodiments, the coated nanoparticle comprises one or more, e.g. 1-3, intermediary layers between the coating and the core. For example, the coated nanoparticle may comprise a core, surrounded by an intermediary layer, which in turn carries the inorganic coating, comprising one or more layers of inorganic material(s).

The Solid Core

The nanoparticle of the invention comprises a solid core comprising at least one biologically active substance (also referred to as biologically active ingredient), optionally in admixture with one or more other substances, e.g. excipients or other biologically active ingredients.

In some preferred embodiments, the nanoparticle solid core is essentially comprised of only biologically active substance(s), i.e. it is free from excipients and any other non-biologically active substances. In some embodiments, the nanoparticle core is essentially comprised of one biologically active substance, e.g. in a crystalline or amorphous state.

The biologically active substance may be selected from any substance which preferably is in solid state, or which may be brought to solid state, at ambient (e.g. room) temperature, e.g. as a crystalline or amorphous material, optionally in combination (e.g. as an admixture or complex) with another substance.

As used herein, the term "biologically active substance" or similar expression, such as "biologically active ingredient" generally refers to any agent, or drug, capable of having a physiologic effect (e.g., a therapeutic or prophylactic effect) on a living subject, e.g. a therapeutically active substance. It also may refer to e.g. a diagnostic agent with no direct therapeutic activity per se, such as a contrast agent for bioimaging.

A biologically active substance according to the invention can be selected e.g. from analgesics, anesthetics, anti-inflammatory agents, anthelmintics, anti-arrhythmic agents, antiasthma agents, antibiotics, anticancer agents, anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products, blood substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radio-pharmaceuticals, hormones, sex hormones, anti-allergic agents, appetite stimulants, anoretics, steroids, sympathomimetics, thyroid agents, vaccines, vasodilators, and xanthines.

In some embodiments, the biologically active substance is a poorly water soluble drug. Non-limiting examples of poorly water soluble drugs which may be used according to the present invention are alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem, or pharmaceutically acceptable salts of any of these.

The person of ordinary skill in the art will be well acquainted with methods for preparing the solid core nanoparticles within the desired size range. This can be performed using nanoparticle growth in wet or dry conditions or by post synthesis manipulation to achieve a nanopowder e.g. using attrition technology such as use of the pearl/ball milling; or by high-pressure homogenization, spray drying, etc., cf. e.g. the Rewiew article: Sivasankar, Mohanty, and B. Pramod Kumar. "Role of nanoparticles in drug delivery system." International Journal of Research in Pharmaceutical and Biomedical Sciences 1 (2010).

The Inorganic Coating

The nanoparticle comprises an inorganic coating typically in the thickness range of 0.1 nm to 5000 nm, e.g. 0.1 nm to 500 nm, or 0.1 nm to 100 nm. For example, the coating may have a thickness ranging from 0.1 nm to 50 nm, or from 0.2 nm to 20 nm, e.g. from 0.5 nm to 10 nm. The coating may be of an essentially uniform thickness over at least part of the surface area of the nanoparticle. In cases where contact holes are formed and covered, the thickness of the coating may vary, e.g. within the above indicated limits.

The coating comprises one or more metals, or metal containing compounds, e.g. metal oxide, metal nitride, metal sulphide, metal selenide, metal carbonates and other ternary compounds etc, and/or one or more metalloids or metalloid containing compounds. For example, the coating may comprise an alkaline metal, an alkaline earth metal, a noble metal, a transition metal, a post-transition metal, or a metalloid, or a mixture of any of these, and/or a compound containing any of these.

While in principle all kinds of coatings such as oxide coating, nitride coating or sulphide coating can be applied to nanoparticle, in a drug delivery application, the coating material preferably should be essentially non-toxic at the amount of nanoparticles administered, and therefore, metal or metalloid oxides generally are preferred.

In some embodiments of the invention the nanoparticle comprises at least one metal oxide layer as an inorganic coating. For example, the nanoparticle may comprise one or several layers of one or more metal oxides. In one embodiment a nanoparticle is provided having a coating that comprises one or more layers, wherein each layer essentially consists of one metal oxide.

In some embodiments, the nanoparticle coating comprises one or more layers composed of mixtures of two or more metal oxides or metalloid oxides. Mixtures of different metal or metalloid oxides in one layer can be used to modify the properties of the layer and to adapt it to the specific demands. Accordingly, another preferred embodiment of the invention is directed to a coated solid nanoparticle comprising a biologically active substance, wherein the coating comprises one or more layers, wherein each layer essentially consists of a mixture of two or more metal or metalloid oxides.

In principle, if the coating comprises more than one layer, each of such layers can be composed of a different metal or metalloid oxide and/or a different mixture of two or more metal or metalloid oxides Advantageously, the metal or metalloids being present in the coating is/are aluminium, titanium, magnesium, iron, gallium, zinc, zirconium and/or silicon, e.g. aluminium, titanium and/or zinc.

Accordingly, in one embodiment, the nanoparticle of the invention is coated with one or more layers containing metals or metalloids, e.g. in the form of oxides or hydroxyoxides, selected from aluminium, titanium, magnesium, iron, gallium, zinc, zirconium, niobium, hafnium, tantalum, lanthanum, and/or silicon; e.g. from aluminium, titanium, magnesium, iron, gallium, zinc, zirconium, and/or silicon, e.g. aluminium, titanium and/or zinc.

More specifically, the present invention is further directed to a coated solid nanoparticle, wherein the metal or metalloid oxide/s is/are selected from the group consisting of aluminium oxide ($Al_2O_3$), titanium dioxide ($TiO_2$), iron oxide ($Fe_xO_y$, e.g. FeO and/or $Fe_2O_3$ and/or $Fe_3O_4$) or a precursor of iron oxide, such as ferrocene ($Fe(C_5H_5)_2$), iron carbonyl ($Fe(CO)_5$), tris(2,2,6,6-tetramethyl-3,5-heptanedionato)iron(III), (dimethylaminomethyl)ferrocene; gallium oxide ($Ga_2O_3$), magnesium oxide (MgO), zinc oxide (ZnO), niobium oxide ($Nb_2O_5$), hafnium oxide ($HfO_2$), tantalum oxide ($Ta_2O_5$), lanthanum oxide ($La_2O_3$), zirconium dioxide ($ZrO_2$) and/or silicon dioxide ($SiO_2$).

In some embodiments, the metal or metalloid oxide/s is/are selected from the group consisting of aluminium oxide ($Al_2O_3$), titanium dioxide ($TiO_2$), iron oxide (FexOy), gallium oxide ($Ga_2O_3$), magnesium oxide (MgO), zinc oxide (ZnO), zirconium dioxide ($ZrO_2$) and/or silicon dioxide ($SiO_2$), e.g. from the group consisting of aluminium oxide ($Al_2O_3$), titanium dioxide ($TiO_2$) and zinc oxide (ZnO).

In some embodiments, the coating consists essentially of $Al_2O_3$. In some other embodiments, the coating consists essentially of $TiO_2$.

The coating preferably is applied to the nanoparticle core, optionally with one or more intermediary layers at the surface by a gas phase technique, which may be either a chemical or physical technique, such as physical vapour deposition (PVD), atomic layer deposition (ALD) also referred to as atomic layer epitaxy (ALE), or other similar techniques, e.g. chemical vapour deposition (CVD).

In a preferred embodiment, ALD is used to coat the nanoparticle core, optionally with one or more intermediary layers at the interface. ALD is a gas phase technique wherein an inorganic coating can be formed on all kinds of surfaces and geometries. One great advantage of ALD is its possibility to completely cover objects with the coating that is applied. In international patent application WO2012/116814, the contents of which is incorporated herein by reference, the use of ALD is disclosed for the coating of solid pharmaceutical preparations, such as pellets, granules, tablets and capsules.

Using ALD, it is possible to obtain ultrathin coatings by deposition of the coating material as monomolecular layers. Depending on the number of reaction cycles one or more atomic layers may be deposited, and coatings of about 0.01 nm to up to about 0.3 nm in thickness per reaction cycle may be deposited.

The ALD coating is formed in a series of two or more self-limited reactions and layers of the coating material may be applied in sequence until a desired coating thickness is achieved.

The coating may be applied at process temperatures from about 20° C. to about 800° C., or from about 40° C. to about 200° C., e.g. from about 40° C. to about 150°, such as from about 50° C. to 100° C. The optimal process temperature depends on the reactivity and/or melting point of the core substance.

In most instances, the first of the consecutive reactions will involve some functional group or free electron pairs or radicals at the surface to be coated, such as a hydroxy group (—OH) or a primary or secondary amino group (—NH$_2$ or —NHR where R e.g. is an aliphatic group, such as an alkyl group). The individual reactions are advantageously carried out separately and under conditions such that all excess reagents and reaction products are removed before conducting the subsequent reaction.

In some embodiments, the biologically active substance may be admixed with a suitable excipient providing the required functionality, e.g. a starch or cellulosic derivative.

Also, the surface of the nanoparticle may be chemically activated prior to applying the inorganic coating, e.g. by treating the nanoparticle with hydrogen peroxide, ozone or by applying a plasma treatment, in order to create free oxygen radicals at the surface of the particle. Thus, in some embodiments, the uncoated nanoparticles, or particles coated with one or more intermediary layers, are immersed in a hydrogen peroxide containing solution prior to applying the inorganic coating.

Before initiating the reaction sequence, the nanoparticle may be treated to remove volatile materials that may be absorbed onto its surface, e.g. by exposing the nanoparticle to vacuum and/or elevated temperature.

Oxide coatings can be prepared on nanoparticles having surface hydroxyl groups (—OH) and/or amine groups (—NH$_2$ or —NHR, where R e.g. is an aliphatic group, such as an alkyl group) using the following binary (AB) reaction sequence:

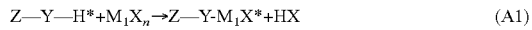

$$Z-Y-H^* + M_1X_n \rightarrow Z-Y-M_1X^* + HX \quad (A1)$$

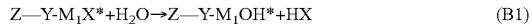

$$Z-Y-M_1X^* + H_2O \rightarrow Z-Y-M_1OH^* + HX \quad (B1)$$

The above reactions are not balanced, and are only intended to illustrate the reactions at the surface of the particle (i.e. not inter- or intralayer reactions). In the reaction scheme, the asterisk (*) indicates the atom that resides at the surface of the particle or coating and Y represents oxygen or nitrogen (NH or NR). In the reaction sequence, $M_1X_n$ is the precursor, wherein $M_1$ is the metal or metalloid atom and X is a displaceable nucleophilic group, e.g. a halogen, such as Cl or Br, or an alkoxy group, such as methoxy.

Specific compounds having the structure $M_1X_n$ that are of particular interest are silicon tetrachloride (SiCl$_4$), tetramethylorthosilicate (Si(OCH$_3$)$_4$), tetraethyl-orthosilicate (Si(OC$_2$H$_5$)$_4$), trimethyl aluminium (Al(CH$_3$)$_3$), triethyl aluminium (Al(C$_2$H$_5$)$_3$), other trialkyl aluminium compounds, bis(ethylcyclopentadienyl) magnesium (Mg(C$_5$H$_4$ C$_2$H$_5$)$_2$), titanium tetraisopropoxide (Ti{OCH(CH$_3$)$_2$}$_4$) and the like.

Specifically preferred are such precursors which allow for conducting the atomic layer deposition at low temperatures, e.g. under 100° C. Such preferred precursors include trimethyl aluminium (Al(CH$_3$)$_3$), bis(ethylcyclopentadienyl) magnesium (Mg(C$_2$H$_5$C$_5$H$_4$)$_2$) and titanium tetraisopropoxide (Ti{OCH(CH$_3$)$_2$}$_4$), titanium tetrachloride (TiCl$_4$) or diethyl zinc (Zn(C$_2$H$_5$)$_2$). Therefore, according to one embodiment of the invention the precursor/s is/are a titanium precursor such as trimethyl aluminium, a magnesium precursor such as bis(ethylcyclopentadienyl) magnesium and/or a titanium precursor such as titanium tetraisopropoxide and titanium tetrachloride or diethyl zinc.

In reaction A1, the precursor $M_1X_n$ reacts with one or more Z—Y—H* groups on the surface of the nanoparticle to create a new surface group having the form -M$_1$-X*. $M_1$ is bonded to the nanoparticle through one or more Y atoms. The -M$_1$-X* group represents a site that can react with water in reaction B1 to regenerate one or more hydroxyl groups. The groups formed in reaction B1 can serve as functional groups through which reactions A1 and B1 can be repeated, each time adding a new layer of $M_1$ atoms. In some cases (such as, e.g., when $M_1$ is silicon, zirconium, titanium, zincum or aluminium) hydroxyl groups can be eliminated as water, forming $M_1$-O-$M_1$ bonds within or between layers. This condensation reaction can be promoted if desired by, for example, annealing at elevated temperatures and/or reduced pressures, cf. also the description in international patent application WO2012/116814 and references cited therein, i.e. A. C. Dillon et al, Surface Science 322, 230 (1995); A. W. Ott et al., Thin Solid Films 292, 135 (1997); Tsapatsis et al. (1991) Ind. Eng. Chem. Res. 30:2152-2159 and Lin et al., (1992), AIChE Journal 38:445-454, which references are all incorporated herein by reference. Following teachings in the above references, coatings of SiO$_2$, Al$_2$O$_3$, ZrO$_2$, TiO$_2$ and B$_2$O$_3$ may be prepared.

In the foregoing reaction sequences, suitable metals and metalloids include silicon, aluminium, titanium, zinc, magnesium and zirconium. Suitable replaceable nucleophilic groups will vary somewhat with M1, but include, for example, fluoride, chloride, bromide, alkoxy, alkyl, acetylacetonate, and the like.

Following ALD as described performance of one cycle results in deposition of one monomolecular layer on the pharmaceutical preparation. If subsequent cycles or series of cycles are performed and the same precursor or different precursors, which contain the same metal, are used in each of these cycles or series of cycles, the whole coating is composed of the same material, which preferably is a metal or metalloid oxide.

The invention is also directed to a method for producing the coated nanoparticle as described herein, the method comprising applying one or more layers of inorganic material to a plurality of said solid cores, and submitting said solid cores to intermittent or continuous disaggregation treatment during or in between application of inorganic material.

It should be noted that according to the present invention, the application of inorganic material to the nanoparticles is a gas phase deposition method. Thus, the particles are not present in a liquid phase or medium during the application of inorganic material.

In one embodiment, the method comprises (a) introducing into a reactor containing the solid nanoparticles to be coated, which is in a gaseous state, (b) purging and/or evacuating the reactor to remove the non-reacted precursors and the gaseous reaction by-products (c) exposing of the second precursor to activate the surface again for the reaction of the first precursor (d) purging and/or evacuating of the reactor and optionally repeating the steps (a) to (d) in order to achieve the desired coating thickness.

As noted herein above, some action must also be taken either to avoid or to compensate for the holes (disruptions) that may result from contact between individual particles during the coating process. Basically, the contact holes may be avoided by keeping the particles in motion during at least part of the coating process, e.g. by use of a fluidized bed, or by submitting the particles to an agitation treatment between sequential applications of inorganic material to the particles, so as to obtain a disaggregation of any particle aggregates formed during application of coating, and/or so as to obtain a rearrangement of particles.

By agitation, as referred to herein, is meant the action of imparting some spatial reorganization of the nanoparticles relative to each other, either continuously as in a fluidized bed, where the particles may be held in more or less constant movement, or intermittently, as in the use of one or more steps of sonication in between consecutive steps of application of inorganic material. The idea is to achieve a spatial rearrangement of the particles with respect to each other, and the skilled person will be able to devise various alternative ways of achieving this without departing from the scope of the present invention.

For example, a convenient method for applying the inorganic coating to the solid is to form a fluidized bed of the nanoparticles, and then pass the various reagents in turn through the fluidized bed under reaction conditions. Methods of fluidizing solid particulate material are well known, and generally include supporting the solid material on a porous plate or screen. A fluidizing gas is passed upwardly through the plate or screen, lifting the material somewhat and expanding the volume of the bed. With appropriate expansion, the solid material behaves much as a fluid. Fluid (gaseous or liquid) reagents can be introduced into the bed for reaction with the surface of the solid nanoparticles. The fluidizing gas also may act as an inert purge gas for removing unreacted reagents and volatile or gaseous reaction products. In this method, contact holes are avoided by the movement of the nanoparticles.

In addition, the reactions can be conducted in a rotating cylindrical vessel or a rotating tube or a reactor chamber with parts that vibrate to keep the particles in movement.

When the particles are coated in a fluidized bed, in a rotating cylindrical vessel or in a rotating tube, or in other apparatus allowing for a more or less random movement of the particles during application of the material, the occurrence of contact holes may be essentially avoided. However, as will be shown in the Examples, and as discussed herein, the uneven coating thickness of particles coated in a method comprising intermediary agitation in between two or more coating steps, in itself may lead to a very advantageous release profile.

In a method where essentially no contact holes are formed, i.e. a method where particles are kept in movement relative to each other during application of the inorganic coating, the coating will have a more even thickness. In such case, the release profile of any one nanoparticle composition or formulation may be suitably adapted by combining nanoparticles of different coating thicknesses and/or of different coating materials.

The Intermediary Layer

Prior to applying the inorganic coating, the nanoparticle core may be subjected to one or more preparatory surface treatments. Thus, one or more intermediary layers of various chemical components may be applied to the surface of the nanoparticle core, e.g. to protect the core from unwanted reactions with precursors during the vapour deposition treatment, to enhance the coating efficiency, or to reduce agglomeration of the nanoparticle cores. It should be realized that while the inorganic coating should provide the nanoparticle with an essentially complete cover, the intermediate layer need not do so.

For example, an intermediary layer may comprise one or more surfactants, in order to reduce agglomeration of the particles to be coated and provide a hydrophilic surface suitable for the subsequent coating. Surfactants that may be applied for this kind of use are well-known to the person of ordinary skill in the art, and may be as well non-ionic, as anionic, cationic or zwitterionic. In some embodiments, the surfactant is a non-ionic surfactant, such as the polyethylene glycol sorbitan esters found in the TWEEN® (Croda International, PLC) series, e.g. polyethylene glycol sorbitan monooleate (or TWEEN® 80).

Thus, in some embodiments, the method of producing a nanoparticle according to the invention comprises a step of surface treatment of the nanoparticle core, prior to the application of the inorganic coating, and this surface treatment may comprise the application of a surfactant to the surface of the core. Such application of a surfactant may be achieved by admixing a surfactant with a liquid phase containing the non-coated nanoparticles (i.e. the solid cores), followed by a lyophilisation, spray drying or other drying method, to provide nanoparticle cores with a surfactant surface layer.

Another example when a preparatory surface treatment of the nanoparticle core may be suitable is when an active ingredient, present in the nanoparticle core, is susceptible to reaction with precursor compounds present in the gas phase during the gas phase coating process (e.g. the ALD process). In such cases, an intermediate layer, e.g. a surfactant layer, also may serve the purpose of protecting the substances from such reaction.

Derivatization or Functionalization of the Nanoparticle

In the nanoparticle of the invention, the core containing active ingredient(s) suitably is entirely covered by the inorganic coating. It is contemplated that the outer surface of the inorganic coating, may be derivatized or functionalized, e.g. by attachment of one or more chemical moieties to the outer surface of the coating, e.g. a compound or moiety of a compound that enhances the targeted delivery of the nanoparticles in the body of the subject (e.g. a mammal, such as a human) to which the nanoparticles are administered. Such compound e.g. may be a polymer, peptide, an antibody, etc.

In some embodiments, the chemical moiety is an anchoring group or "handle", such as a group containing a silane function. Silanization of a metal and e.g. metal oxide of hydroxyoxide surface is a well-known method for attaching functional groups to such a surface, and examples are described e.g. by Herrera A. P. et al., in J. Mater. Chem., 2008, 18, 3650-3654, and in U.S. Pat. No. 8,097,742 B2.

To this anchoring group, any desired compound, e.g. the desired targeting compound may be attached. Thus, in some embodiments, a nanoparticle according to the invention is provided, having a solid core, optionally one or more intermediary layers, said core and optional intermediary layers covered by an inorganic coating, wherein anchoring groups are attached to the outer surface of said inorganic coating, said anchoring groups being capable of binding at least one targeting molecule. The binding of the targeting molecule may be accomplished by covalent binding or by non-covalent binding, e.g. ionic binding, hydrogen bonding or van der Waals bonding, or a combination of different types of binding.

The nanoparticles with anchoring groups will provide a versatile tool for targeted delivery to various parts of the body, by attaching an appropriate targeting molecule to said nanoparticle. As noted already, such targeting molecule e.g. may be a polymer, peptide, a protein, a nucleic acid. For example, the targeting molecule may be an antibody or antibody fragment, or a receptor-binding protein or peptide.

In one further embodiment, a kit is provided, comprising nanoparticles as described herein, having anchoring groups, e.g. groups containing silane functions, attached to the outer surface of the inorganic coating. In some embodiments, such kit also contains at least one reagent useful for attaching target molecules to said anchoring groups and optionally an instructional material, e.g. a leaflet with written instructions of how to use the kit. In some embodiments, the kit also contains at least one targeting molecule suitable for being attached to the nanoparticle via the anchoring group.

The Pharmaceutical Formulation and its Use

According to one aspect, the present invention relates to a nanoparticle as defined herein for use in the medical field, e.g. in therapy or as a diagnostic tool. By means of the coated nanoparticle of the invention, it will be possible to formulate a large diversity of pharmaceutically active compounds, including poorly soluble compounds that previously have been difficult to formulate correctly or that may have been hampered by poor biodistribution. For example, depending on the active ingredient included in the nanoparticle of the invention, the nanoparticles of the invention may be used in the treatment disorders, such as various types of cancers, inflammatory disorders, neurodegenerative disorders, autoimmune disorders etc.

Thus, according to one aspect, the invention relates to a pharmaceutical formulation comprising a plurality of nanoparticles according to the invention. The formulation may be suitable for topical or systemic, parenteral or enteral, e.g. oral or rectal, administration and comprises a therapeutically effective amount of nanoparticles according to the invention, where each nanoparticle consists of an active ingredient forming or included in a nanoparticle core surrounded by an inorganic coating as defined herein. The pharmaceutical formulation in addition may comprise a pharmaceutically acceptable excipient, e.g. a pharmaceutically acceptable carrier for the nanoparticles. In general the therapeutically effective amount will vary depending on the active ingredient included in the nanoparticles, the disease state being treated, the severity of the disease treated, the age and relative health of the subject, the route and form of administration, the judgment of the attending medical or veterinary practitioner, etc.

As used herein, an "effective amount" of nanoparticles or of biologically active agent is that amount effective to bring about the physiological change desired in the subject to which the nanoparticles are administered. The term "therapeutically effective amount" as used herein, means that amount of nanoparticles or of biologically active agent, alone or in combination with another agent according to the particular aspect of the invention, that elicits the biological or medicinal response in the subject to which the nanoparticles of the invention are administered, e.g. alleviation of the symptoms of the disease or disorder being treated, or curing or preventing the disease or the disorder.

The pharmaceutical formulation of the invention may comprise nanoparticles of different type. For example, a pharmaceutical formulation may comprise particles of different sizes, e.g. an amount of nanoparticles having a size within one size range in combination with an amount of nanoparticles having a size within another size range. The different size ranges may be due to different sizes of the cores, or different thicknesses of the coatings, or a combination of both.

Thus, in some embodiments, there is provided a pharmaceutical formulation comprising an amount of nanoparticles having a thin inorganic coating, or even having no inorganic coating, in combination with an amount of nanoparticles having a thicker inorganic coating. By combining, in one and the same formulation, nanoparticles with different coating thicknesses and/or different core sizes, the drug release obtained in the body of the treated subject may be extended over a selected time period, e.g. from nearly instant release to prolonged release.

In some embodiments, therefore, the pharmaceutical formulation comprises nanoparticles of different active ingredients and/or of different release profiles. For example, in some embodiments, the formulation comprises an amount of nanoparticles having a coating of a thickness that allows for release of a first substance over a first period of time, and an amount of nanoparticles having a coating of another, greater, thickness that allows for release of a second substance over a second period of time, which second period may be overlapping with the first period of time or not.

In other embodiments, the pharmaceutical formulation of the invention comprises nanoparticles having different functionalization or derivatization at the nanoparticle surface. For example, a pharmaceutical formulation of the invention may comprise an amount of nanoparticles functionalized with one type of targeting molecule, directing the nanoparticles to one organ or cell type in the body, and an amount of nanoparticles functionalized with another type of targeting molecule, directing the nanoparticles to the same or another organ or cell type in the body.

For enteral, e.g. oral, administration, the nanoparticles of the invention may be formulated in a wide variety of dosage forms. The pharmaceutically acceptable carriers may be either solid or liquid. Solid form preparations include granules (wherein each granule consists of several nanoparticles and e.g. a binder), tablets, pills, lozenges, capsules, cachets, suppositories. A solid carrier may be one or more substances which may also act as e.g. diluents, flavouring agents, lubricants, binders, preservatives, tablet disintegrating agents, or an encapsulating material. In tablets, the nanoparticles of the invention generally are mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like.

In another embodiment, the nanoparticles are encapsulated e.g. in a soft or hard shell capsule, e.g. a gelatine capsule.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the nanoparticles.

The nanoparticles of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension of the inventive nanoparticles. This suspension may be formulated according to techniques known in the art using suitable dispersing or wetting agents (e.g., polyethylene glycol sorbitan monooleate, or TWEEN® 80), and suspending agents. The sterile injectable or infusible preparation may also be a sterile injectable or infusible suspension in a non-toxic parenterally-acceptable diluent. For example, the pharmaceutical composition may be a solution in 1,3-butanediol. Other examples of acceptable vehicles that may be employed in the compositions of the present invention include, but are not limited to, mannitol, water, Ringer's solution and isotonic sodium chloride solution. In addition, sterile, fixed oils may be employed as a suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil suspensions may also contain a long-chain alcohol diluent or dispersant.

In some embodiments, the pharmaceutical composition of the invention is a formulation suitable for inhalation, e.g. an inhalation powder such as may be administered by use of dry powder inhalers. This type of formulations are described e.g. by Kumaresan C., et al in Pharma Times—Vol. 44—No. 10—October 2012, pp 14-18 and in by Mack P., et al., in Inhalation, vol. 6, No. 4, August 2012, pp. 16-20, the contents of which are incorporated herein by reference.

In such embodiments, the size of the nanoparticle suitably is in the range having a diameter of from about 20 µm to 50 µm.

In some embodiments, of an inhalation formulation of the invention, the drug release from the formulation may be controlled so as to give in one and the same dosage, immediate or quick release and prolonged release. This is achieved by combining particles having different coatings, e.g. varying e.g. in thickness, and optionally also particles without coating. For example, particles having no coating may be combined with particles having a coating of e.g. 5 nm, which after inhalation start to dissolve after e.g. 30 minutes, and optionally also particles with an even thicker coating, which after inhalation start to dissolve after a much longer time period, e.g. of several days.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery, containing the nanoparticles of the invention. The composition may be formulated with a suitable ointment containing the inventive nanoparticles suspended in a carrier, such as mineral oil, liquid petroleum, white petroleum, propylene glycol, polyoxyethylene polyoxypropylene compound, emulsifying wax and water. Alternatively, the pharmaceutical composition may be formulated with a suitable lotion or cream containing the nanoparticles of the invention in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

In some embodiments, a pharmaceutical composition of the invention may comprise from approximately 1% to approximately 99%, preferably from approximately 20% to approximately 90% of nanoparticles of the invention, together with at least one pharmaceutically acceptable excipient.

The nanoparticle of the invention and its use are further illustrated in the accompanying drawings. In these drawings, FIG. 1 represents a nanoparticle 1 comprising a solid core 2 enclosed by a coating 3. While the particle represented in FIG. 1 is spherical, it should be realized that this is of course merely a schematic representation, and in fact the nanoparticle 1 may also be irregular in shape. Likewise, the proportions between the nanoparticle diameter and the coating thickness are merely illustrative and these proportions may vary depending on factors such as the desired dissolution time, the numbers of layers in the coating, etc.

Figure 2:
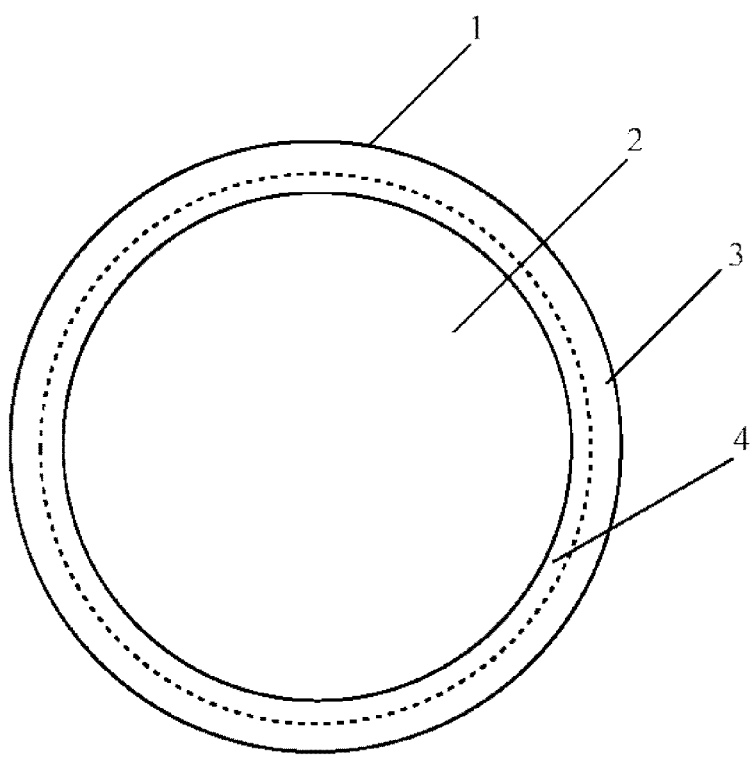
FIG. 2 illustrates another nanoparticle of the invention, having a core comprising a biologically active substance, said core being surrounded by an inorganic coating, and an intermediate layer between the core and coating, said intermediate layer having a chemical composition different from that of the core and that of the inorganic coating.

The nanoparticle 1 represented in FIG. 2 comprises an intermediary layer 4, between the core 2 and the coating 3. This intermediary layer 4 may enclose and cover entirely the core 2 or not, depending e.g. on the purpose of the layer, which is illustrated by the broken line in FIG. 2.

Figure 3:
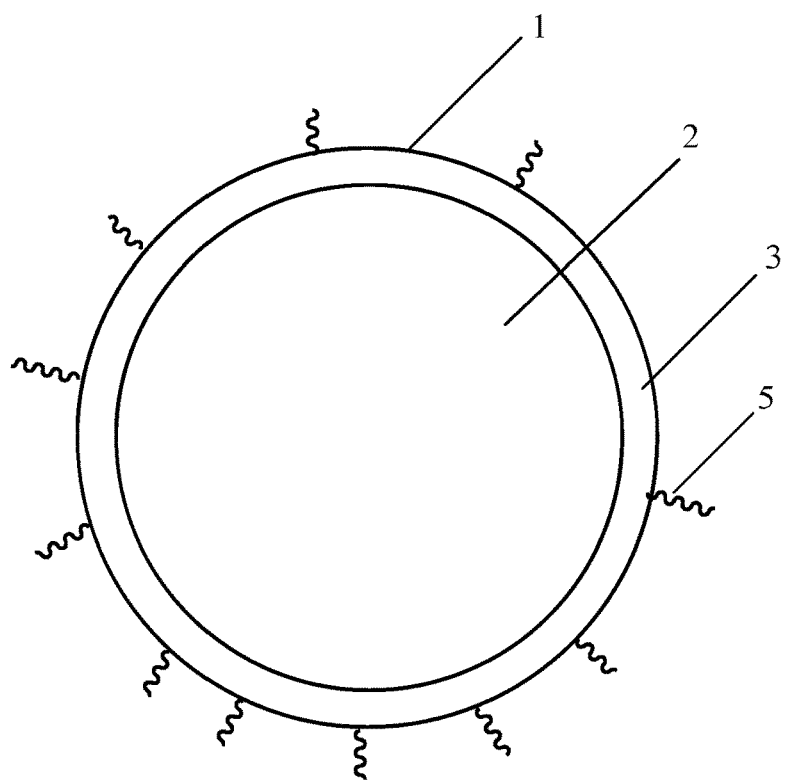
FIG. 3 illustrates another nanoparticle of the invention, having a core comprising a biologically active substance, said core being surrounded (or enclosed) by an inorganic coating, said coating having chemical moieties attached to the outer surface of the inorganic coating.

The nanoparticle 1 represented in FIG. 3 comprises chemical moieties 5 attached to the outer surface of the inorganic coating 3, e.g. anchoring groups permitting to attach another molecule to the surface, such as a targeting molecule. The chemical moiety 5 also may be a moiety fulfilling in itself a purpose such as targeting of an organ or cell type in the body of a subject to which the nanoparticle is administered.

While the nanoparticle 1 shown in FIG. 3 does not comprise any intermediary layer of the type illustrated in FIG. 2, it should be realized that such variant is also contemplated.

Figure 4:
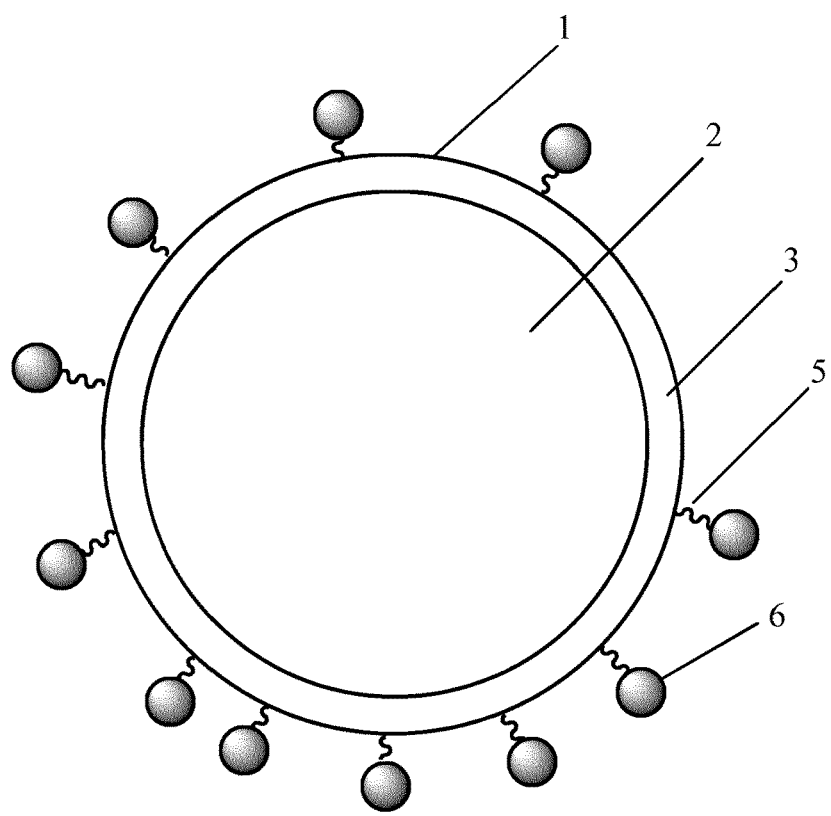
FIG. 4 illustrates another nanoparticle of the invention, having a core comprising a biologically active substance, said core being surrounded by an inorganic coating, said coating having chemical moieties attached to the outer surface of the inorganic coating, the chemical moieties being anchoring groups capable of binding a selected molecule, such as a targeting molecule.

In FIG. 4, a nanoparticle 1 is shown having a chemical moiety 5 which is an anchoring group, to which anchoring group a selected molecule 6 is bound. As for the nanoparticle of FIG. 3, it is contemplated a variant of the nanoparticle of FIG. 4 comprises at least one intermediary layer between the inorganic coating 3 and the solid core 2.

In the embodiments represented in FIGS. 1-4, the inorganic coating also may comprise several layers of different compositions, e.g. one layer of $Al_2O_3$ and one layer of $TiO_2$.

Figure 5:
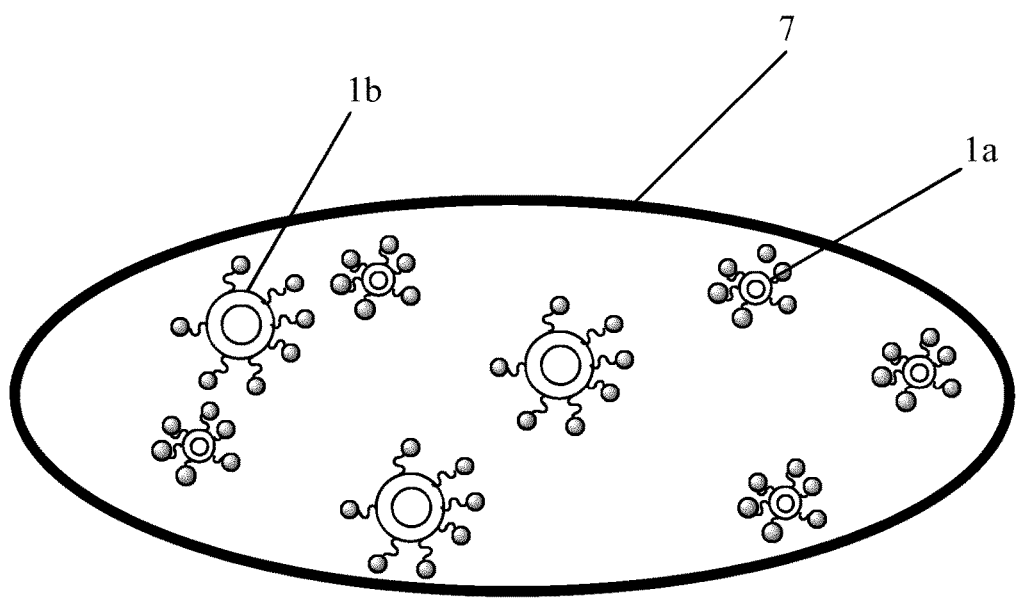
FIG. 5 illustrates a pharmaceutical dosage unit comprising an amount of one type of nanoparticle according to the invention in combination with an amount of another type of nanoparticle according to the invention.

Finally, in FIG. 5 a pharmaceutical dosage unit 7 according to the invention is illustrated, containing an amount of a first nanoparticle 1a and an amount of a second nanoparticle 1b. In FIG. 5, the nanoparticles are schematically shown as differing in size of both core and coating. It should be realized that also the chemical composition of the nanoparticles may differ, as may the surface functionalization. The dosage unit may be e.g. a capsule. In addition to the nanoparticles of the invention the dosage unit may comprise also other active ingredients, in particulate or non-particulate form as well as pharmaceutically acceptable excipients.

The invention will now be further described by the following non-limiting examples.

EXAMPLES

Example 1

A powder of a drug has grain sizes of 100 nm. A problem with the drug is that it cannot be administered into a patient orally and maintain its optimal medical effect. It would be more favourable if the drug could reach its destination in the body as a relatively inert nanoparticle before the release of the drug. To achieve this, a thin coating of alumina ($Al_2O_3$) is applied to the grains/powder using ALD. The alumina prevents the powder from being dissolved directly in the body and the thickness of the coating determines how long the dissolution will take. Dissolution of alumina is possible by presence of chloride ions even in acidic and neutral pH.

The process to form the alumina coating by ALD is performed at a temperature of 50-100° C. and the drug withstand that temperature without being deteriorated.

Example 2

A powder of a drug has grain sizes of 1000 nm. A problem with the drug is that its surface is terminated by polar functional groups, preventing transport through cell membranes. By applying a thin coating of titanium dioxide ($TiO_2$) on the surface of the grains this problem can be circumvented since titanium oxide provides another chemical composition of its surface than the drug.

The process to form the titanium oxide coating by ALD is performed at a temperature of 100-150° C. and the drug withstands that temperature without being deteriorated.

Example 3

A powder of a drug has a size of 100 nm. A problem with the drug is that it cannot be modified with the desired molecules for targeting or other functions. Coating the grains with a thin film of alumina ($Al_2O_3$) on which the desired molecules for targeting or other functions can be coupled circumvents the problem.

Example 4

A powder of a drug has a size of 200 nm. The powder is admixed with an aqueous solution of polyethylene glycol sorbitan monooleate (TWEEN® 80) and allowed to dry. To the powder with surfactant treated surface, a thin coating of alumina ($Al_2O_3$) is applied.

Example 5

A particle powder (0.3 g, approximate particle size 150 nm) of felodipine (i.e. (RS)-3-ethyl 5-methyl 4-(2,3-dichlorophenyl)-2,6-dimethyl-1,4-dihydropyridine-3,5-dicarboxylate) was placed in a 5 cm² tray and the tray was introduced into an ALD reaction chamber. The reactor was heated to a temperature of 50-100° C. ALD was performed using trimethyl aluminium and water as ALD precursors. 50 ALD cycles were performed with ALD pulse lengths of 1-10 seconds. The obtained product consisted of particles having a coating of about 3 nm thickness, except at points of contact between individual particles.

The felodipine particle powder was discharged from the reactor, placed in 5 ml of water and sonicated for 5 minutes. Felodipine has very low water solubility, and therefore water was selected as a liquid phase (dispersion medium) for the sonication step. The sonication resulted in a deagglomeration with breaking up of the contact points between individual felodipine particles.

The felodipine particle powder was allowed to settle in the water and excess water was decanted. The powder was then allowed to dry. The powder was "fluffed" using a spatula and placed once again in the tray for loading into the reactor.

The steps of ALD coating of the powder, sonication of the powder, and drying of the sonicated powder were repeated 3 times, to a total of 4 cycles. The obtained dry powder was free-flowing and the main fraction (more than 50% of the particles) had a 10-20 nm thick aluminum oxide coating without disruptions (contact holes).

Example 6

A particle powder (0.3 g, approximate particle size 30 µm) of paracetamol (i.e. N-(4-hydroxifenyl)acetamid) was placed in a 5 cm² tray and the tray was introduced into an ALD reaction chamber. The reactor was heated to a temperature of 50-100° C. ALD was performed using trimethyl aluminium and water as ALD precursors. 50 ALD cycles were performed with ALD pulse lengths of 1-10 seconds. The obtained product consisted of particles having a coating of about 3 nm thickness, except at points of contact between individual particles.

The paracetamol particle powder was discharged from the reactor, placed in 5 ml of heptanol and sonicated for 5 minutes. Paracetamol has high water solubility but low solubility in e.g. heptane, and therefore heptane was selected as a liquid phase (dispersion medium) for the sonication step. The sonication resulted in a deagglomeration with breaking up of the contact points between individual paracetamol particles.

The paracetamol particle powder was allowed to settle and excess heptane was decanted. The powder was then allowed to dry. The powder was "fluffed" using a spatula and placed once again in the tray for loading into the reactor.

The steps of ALD coating of the powder, sonication of the powder and drying of the sonicated powder were repeated 4 times, to a total number of 5 cycles. After the last drying step, the obtained powder was free-flowing and the main fraction (more than 50% of the particles) had a 10-20 nm thick aluminum oxide coating without disruptions (contact holes).

Example 7

A particle powder (0.03 g, approximate particle size 150 nm) of felodipine is placed in a 5 cm² tray and the tray is introduced into an ALD reaction chamber. The reactor is heated to a temperature of 50-100° C. ALD is performed using trimethyl aluminium and water as ALD precursors. 10-30 ALD cycles are performed with ALD pulse lengths of 0.1-450 seconds. The obtained product consists of particles having a coating of about 0.5-2 nm thickness, except at points of contact between individual particles.

The felodipine particle powder is discharged from the reactor, placed in 5 ml water and sonicated for 5 minutes.

After 5 minutes of sonication, the powder is allowed to settle and excess water is decanted. The powder is then allowed to dry. The powder is "fluffed" using a spatula and placed once again in the tray for loading into the reactor.

The steps of ALD coating of the powder, sonication of the powder, and drying of the sonicated powder are repeated 3 times, i.e. a total of 4 series, each series comprising a deposition step including 50 ALD cycles, followed by a step of sonication and drying of the sonicated particles. The obtained dry powder is free-flowing and has a 2-8 nm thick aluminum oxide coating without disruptions (contact holes).

The felodipine containing nanoparticles having a non-disrupted coating can if necessary be separated from any remaining incompletely covered nanoparticles by soaking of the powder in dichloromethane, which is a solvent for felodipine, separating the soaked particles from the soaking medium, and optionally rinsing the separated particles.

The precursors are thereafter changed to titanium tetrachloride and water ALD is performed on the aluminium oxide coated felodipine particles, using essentially same conditions as in the previous ALD treatment (reactor temperature 50-100° C., 10-30 ALD cycles, ALD pulse lengths of 1-10 seconds), so as to form a coating of titanium oxide on top of the aluminum oxide coating. In this second sequence of ALD treatment and deagglomeration treatment, the series are performed in total 4 times.

Example 8

The procedure of Example 5 is followed, but the series of ALD treatment and deagglomeration treatment are performed 8 times. A felodipine nanoparticle powder is obtained with a 15 nm thick coating of aluminium oxide, and a particle size of 40 µm.

Example 9

The procedure of Example 6 was followed, but the series of ALD treatment and deagglomeration treatment were performed 8 times in total. A paracetamol nanoparticle powder was obtained, having 15 nm thick coating of aluminium oxide and a particle size of 40 µm.

Example 10

The procedure of Example 5 is followed, but titanium tetrachloride and water are used as precursors in the ALD treatment. A felodipine nanoparticle powder is obtained with a 15 nm thick coating of titanium oxide, and a particle size of 40 µm.

Example 11

The procedure of Example 6 is followed, but titanium tetrachloride and water are used as precursors in the ALD treatment. A paracetamol nanoparticle powder is obtained with a 5 nm thick coating of titanium oxide, and a particle size of 150 nm.

Comparative Example 12

The procedure of Example 6 was followed, but after the first sonication and drying of the ALD treated nanoparticles, the dry powder was collected, without any further application of inorganic coating.

Example 13

About 15 mg of the coated paracetamol nanoparticles prepared in Example 6 were admixed with 100 ml of deionized water and then sonicated for 5 minutes. The mixture was diluted to 1 liter by addition of more deionized water and was stirred using a magnetic stirrer. Samples of the supernatant (water containing dissolved paracetamol) were taken at regular intervals and the absorbance at 243 nm was measured as an indication of the paracetamol concentration in the supernatant.

Example 14

The procedure of Example 13 was repeated using the coated paracetamol nanoparticles of Example 9.

Comparative Example 15

The procedure of Example 13 was repeated using the paracetamol nanoparticles of Comparative Example 12.

Figure 6:
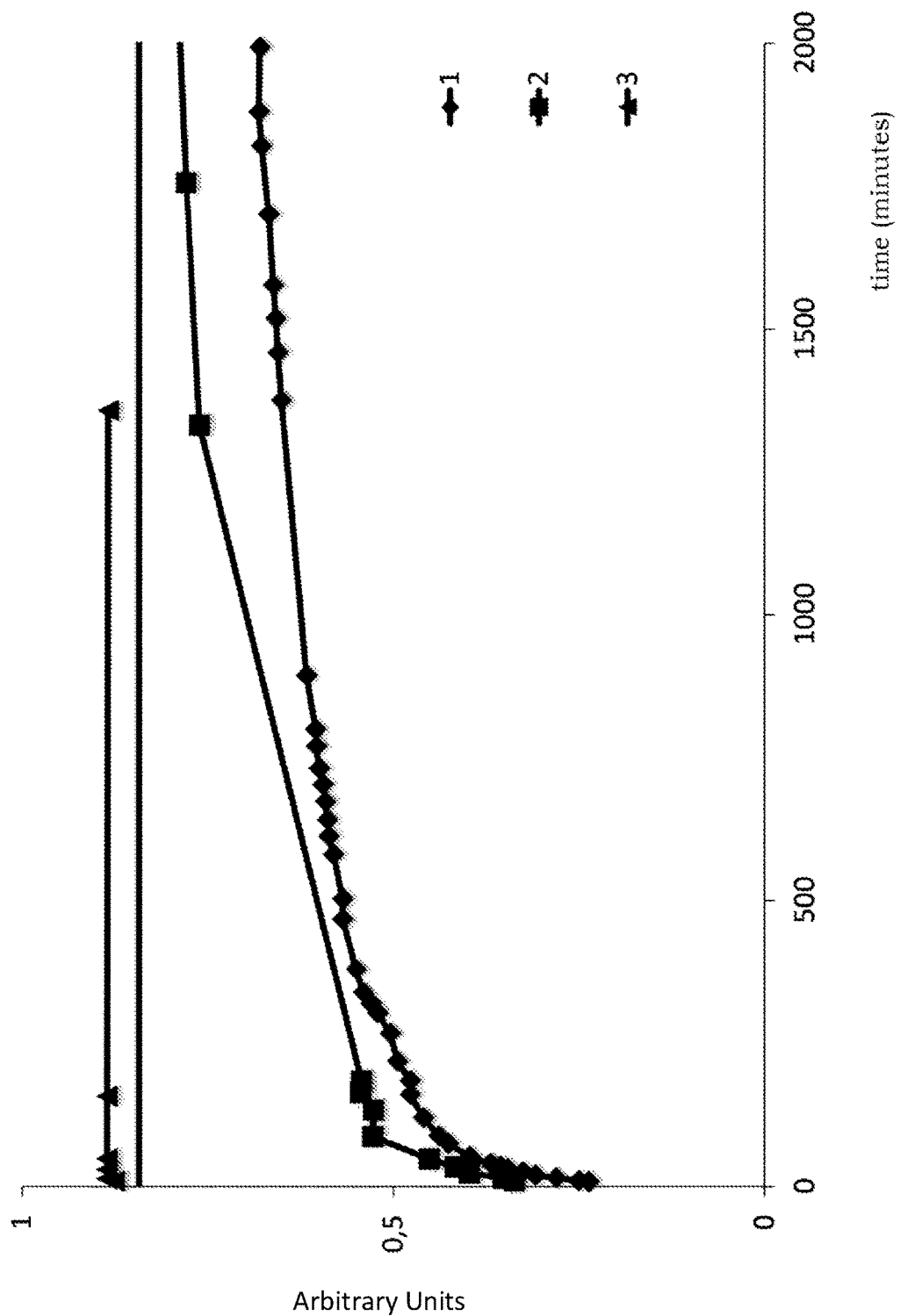
FIG. 6 illustrates aqueous dissolution profiles of nanoparticles consisting of a paracetamol solid core coated by $Al_2O_3$, prepared by an intermittent agitation method comprising 8 and 5 series, respectively, of applying inorganic material and subsequent agitation; and of nanoparticles consisting of a paracetamol solid core coated by $Al_2O_3$, prepared by a method comprising 1 serie of applying inorganic material and subsequent agitation. The graphs are identified as follows: Filled Diamond 1: 8 series; Square 2: 5 series; Triangle 3: 1 series.

In FIG. 6 the results of the dissolution tests of Examples 13-15 are shown. In FIG. 6, the diamonds 1 show the results obtained in Example 14 (8 coating/agitation series); the squares 2 show the results obtained in Example 13 (5 coating/agitation series); and the triangles 3 show the results obtained in Comparative Example 15 (1 coating/agitation series). The straight, horizontal line with no marking (at about 0.8) represents the concentration of paracetamol in the aqueous phase at total dissolution of the coated nanoparticles of Examples 6 and 9.

From the results, it appears that the coated nanoparticles of the invention have a profile of substantially delayed dissolution. Moreover, the delay may be tailored varying the number of ALD (or other deposition) cycles and the number of series comprising ALD (or other coating) treatment with intermediate agitation treatment.

Without wishing to be bound to any theory, it is considered that normally, the release of the solid core from any one particle is an instantaneous event, occurring after a delay which increases with the thickness of the coating surrounding the solid core (i.e. the thicker the coating, the longer the time for its disintegration or dissolution). Paracetamol is a very water soluble substance and in theory, therefore, a plurality of nanoparticles having a uniform coating thickness, could be expected to show a dissolution profile of paracetamol in an aqueous liquid phase comprising an initial lag time during which the coating slowly dissolves in the liquid phase, followed by a short period of rapid increase of the paracetamol concentration in the liquid phase, corresponding to rapid dissolution of paracetamol at the time point where the surrounding coating has dissolved enough to provide access of the water to the paracetamol. In contrast to this theoretical dissolution profile, the nanoparticles of the inventions show a rapid rise, followed by a slow and steady rise, of the paracetamol concentration in the liquid phase.

The rapid rise of paracetamol concentration during the first few minutes are considered to correspond to remaining incompletely encapsulated nanoparticles, from which paracetamol is quickly dissolved. This supposition is supported by the fact the maximum level of the initial rapid increase of paracetamol concentration in the supernatant decreases as the number of coating series increases. Increasing the number of series of coating and deagglomeration will lead to an increased fraction of completely covered nanoparticles.

The subsequent slow rise of paracetamol concentration in the supernatant is considered to be the result of the uneven coating of the nanoparticles. Again without wishing to be bound to any theory, it may be surmised that during each application of coating, new contact points between particles will arise in a random manner, and thereby each particle will have a coating of varying thickness over its surface. Dissolution of a plurality of such particles having uneven surface coatings will result in the slowly rising concentration profile obtained by Examples 13 and 14. In an in vivo administration, nanoparticles of Example 6 and 9, will be able to provide a delayed release of paracetamol in the body of the treated subject.

It should be noted that incompletely coated nanoparticles, such as those giving rise to the initial rapid rise in paracetamol in Examples 13 and 14, may easily be eliminated from the nanoparticle product obtained at the end of the coating process, e.g. by bringing the product in contact with a solvent for the nanoparticle solid core. For example, nanoparticles having a water soluble solid core may be washed with water or an aqueous solution and allowed to dry. Particles with a non-water soluble solid core, e.g. a core soluble in organic solvent, may be washed with such organic solvent. In the washing step(s), the solid core of the incompletely coated nanoparticles will dissolve and particles having a completely enclosed solid core may thereafter be separated from the liquid phase, and optionally rinsed and dried.

Thus, in some embodiments the present invention provides a method of preparing a plurality of nanoparticles, each particle having a solid core comprising a biologically active substance, said core being enclosed by an inorganic coating, the method comprising the steps of applying one or more layers of inorganic material to said solid cores, submitting said solid cores to agitation during and/or in between application of the layers of inorganic material, and bringing the obtained nanoparticles into contact with a solvent for the solid core.

In the step of eliminating incompletely coated nanoparticles, the solvent for the solid core preferably should not be a solvent for the inorganic coating, or should be only a poor solvent for the inorganic coating.

Very advantageously, by the method of the invention, nanoparticle compositions may be provided having a desired controlled release profile, e.g. a delayed release profile, a sustained release profile etc. In some embodiments, the method therefore comprises:

bringing a sample of the coated nanoparticles into contact with a liquid phase which is a solvent for the solid core and for the inorganic coating, measuring dissolution of the coated nanoparticle solid cores in the liquid phase, comparing the dissolution of coated nanoparticle solid cores with the dissolution of similar solid cores having no inorganic coating, determining a delay in dissolution of the coated nanoparticle solid cores compared to the dissolution of similar solid cores having no inorganic coating, and selecting coated nanoparticles having a delay in dissolution exceeding a predetermined length of time.

The liquid phase which is a solvent for the solid core and for the inorganic coating e.g. may be water, an aqueous solution, a phosphate buffer or any other suitable liquid.

The dissolution of the coated nanoparticles in the liquid phase may be measured e.g. by determining the concentration of the active substance in the liquid phase.

The dissolution profile of coated nanoparticle solid cores is compared to the dissolution profile of similar solid cores having no inorganic coating in order to provide information about the delay in dissolution provided by the coating.

For example, the delay in dissolution may be determined as the difference between the time needed to dissolve at least 50% by weight, of the coated nanoparticle solid cores and the time needed to dissolve at least 50% by weight of the solid cores having no coating.

In some embodiments, the delay in dissolution is determined as the difference between the time needed to dissolve at least 90% by weight, of the coated nanoparticle solid cores and the time needed to dissolve at least 90% by weight of the solid cores having no coating.

In some embodiments, the delay in dissolution is determined as the difference between the time needed to dissolve at least 95% by weight, of the coated nanoparticle solid cores and the time needed to dissolve at least 95% by weight of the solid cores having no coating.

In some embodiments, the delay in dissolution is determined as the difference between the time needed to dissolve at least 99% by weight, of the coated nanoparticle solid cores and the time needed to dissolve at least 99% by weight of the solid cores having no coating.

In some embodiments, the delay in dissolution is determined as the difference between the time needed to dissolve 100% by weight, of the coated nanoparticle solid cores and the time needed to dissolve 100% by weight of the solid cores having no coating.

Coated nanoparticles having a delay in dissolution exceeding a predetermined length of time may thus be suitably selected. If the delay in dissolution is considered insufficient according to the test, parameters of the method, e.g. the number of applications of inorganic material to the nanoparticles may be increased so as to provide a thicker coating, or the inorganic material may be changed, etc.

Very advantageously, the present invention thus provides for a method of obtaining a pharmaceutical formulation with a fine tuning of release properties. Moreover, nanoparticles of different release profiles may be combined in one and the same pharmaceutical formulation, which increases even further the possibility of varying the release profile of the formulation.

The invention claimed is:

1. A method of preparing a controlled or delayed release pharmaceutical composition comprising:
   i. a plurality of coated particles of a size that is from 0.1 μm to 50 μm, said coated particles having a solid core comprising a biologically active substance, said solid core being enclosed by one or more metal oxide materials; and
   ii. a pharmaceutically acceptable carrier,
   the method comprising the sequential steps of:
   (1) applying an initial coating of at least one metal oxide to said solid cores in an atomic layer deposition reactor;
   (2) discharging the coated particles from the reactor and subjecting the coated particles to agitation to disaggregate particle aggregates formed during step (1);
   (3) reintroducing the disaggregated, coated particles from step (2) into an atomic layer deposition reactor and applying a further coating of at least one metal oxide to the reintroduced particles;
   (4) optionally repeating steps (2) and (3) one or more times to increase total thickness of the one or more metal oxide materials that enclose said solid core; and
   (5) admixing said coated particles obtained from step (3) or step (4) with said pharmaceutically acceptable carrier to form said pharmaceutical composition.

2. The method of claim 1, wherein steps (2) and (3) are repeated at least once.

3. The method of claim 1, wherein steps (2) and (3) are repeated at least twice.

4. The method of claim 1, wherein steps (2) and (3) are repeated three times.

5. The method of claim 1, wherein steps (2) and (3) are repeated up to nine times.

6. The method of claim 1, wherein the one or more metal oxide materials comprise aluminum oxide, titanium dioxide, iron oxide, gallium oxide, magnesium oxide, zinc oxide, niobium oxide, hafnium oxide, tantalum oxide, lanthanum oxide, zirconium dioxide, and/or silicon dioxide.

7. The method of claim 1, wherein the one or more metal oxide materials comprise aluminium oxide, titanium dioxide and/or zinc oxide.

8. The method of claim 1, wherein the solid core consists essentially of the biologically active substance.

9. The method of claim 1, wherein the total thickness of all the metal oxide coatings is from 0.1 nm to 500 nm.

10. The method of claim 1, wherein the total thickness of all the metal oxide coatings is from 0.1 nm to 100 nm.

11. The method of claim 1, wherein the total thickness of all the metal oxide coatings is from 0.1 nm to 50 nm.

12. The method of claim 1, wherein the biologically active substance is selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a protein, a peptide, a polypeptide, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

13. The method of claim 1, wherein the biologically active substance is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem and pharmaceutically acceptable salts of any of these agents.

14. The method of claim 1, wherein the biologically-active substance in the solid core is either in admixture with one or more other substances selected from excipients and other biologically-active ingredients, or is free from said other substances.

15. A controlled or delayed release pharmaceutical composition comprising:
  i. a plurality of coated particles of a size that is from 0.1 μm to 50 μm, said coated particles having a solid core comprising a biologically active substance, said solid core being enclosed by one or more metal oxide materials to enable a therapeutically effective controlled or delayed release of the biologically active substance from the coated particles in said pharmaceutical composition; and
  ii. a pharmaceutically acceptable carrier,
  the pharmaceutical composition being prepared according to a process comprising the sequential steps of:
    (1) applying a coating of at least one metal oxide to said solid cores in an atomic layer deposition reactor;
    (2) discharging the coated particles from the reactor and subjecting the coated particles to agitation to disaggregate particle aggregates formed during step (1);
    (3) reintroducing the disaggregated, coated particles from step (2) into an atomic layer deposition reactor and applying a further coating of at least one metal oxide to the reintroduced particles;
    (4) optionally repeating steps (2) and (3) one or more times to increase total thickness of the one or more metal oxide materials that enclose said solid core; and
    (5) admixing said coated particles obtained from step (3) or step (4) with said pharmaceutically acceptable carrier to form said pharmaceutical composition
  wherein the controlled or delayed release of the biologically active substance from the coated particles is provided by the process steps (1) to (3) and (4), if performed.

16. The pharmaceutical composition of claim 15, wherein the pharmaceutically acceptable carrier is in the form of a solid.

17. The pharmaceutical composition of claim 15, wherein steps (2) and (3) are repeated at least once.

18. The pharmaceutical composition of claim 15, wherein steps (2) and (3) are repeated at least twice.

19. The pharmaceutical composition of claim 15, wherein steps (2) and (3) are repeated three times.

20. The pharmaceutical composition of claim 15, wherein steps (2) and (3) are repeated up to nine times.

21. The pharmaceutical composition of claim 15, wherein the one or more metal oxide materials comprise aluminum oxide, titanium dioxide, iron oxide, gallium oxide, magnesium oxide, zinc oxide, niobium oxide, hafnium oxide, tantalum oxide, lanthanum oxide, zirconium dioxide, and/or silicon dioxide.

22. The pharmaceutical composition of claim 15, wherein the one or more metal oxide materials comprise aluminium oxide, titanium dioxide and/or zinc oxide.

23. The pharmaceutical composition of claim 15, wherein the solid core consists essentially of the biologically active substance.

24. The pharmaceutical composition of claim 15, wherein the total thickness of all the metal oxide coatings is from 0.1 nm to 500 nm.

25. The pharmaceutical composition of claim 15, wherein the total thickness of all the metal oxide coatings is from 0.1 nm to 100 nm.

26. The pharmaceutical composition of claim 15, wherein the total thickness of all the metal oxide coatings is from 0.1 nm to 50 nm.

27. The pharmaceutical composition of claim 15, wherein the biologically active substance is selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a protein, a peptide, a polypeptide, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

28. The pharmaceutical composition of claim 15, wherein the biologically active substance is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem and pharmaceutically acceptable salts of any of these agents.

29. The pharmaceutical composition of claim 15, wherein the biologically-active substance in the solid core is either in admixture with one or more other substances selected from excipients and other biologically-active ingredients, or is free from said other substances.

\* \* \* \* \*